Figure 1:
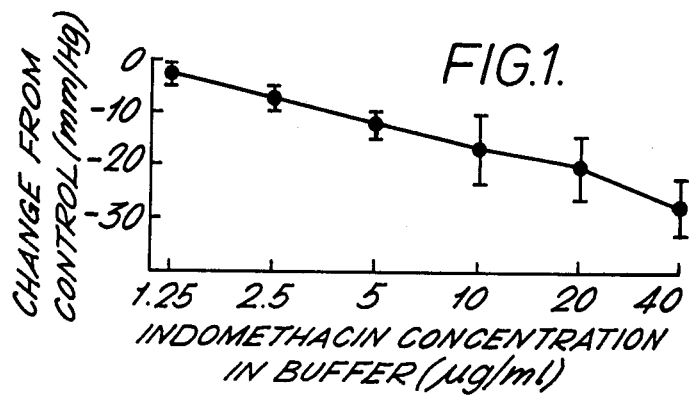

United States Patent [19]

Horrobin

[11] 4,287,202

[45] Sep. 1, 1981

[54] TREATMENT AND/OR PROPHYLAXIS OF SPASMS OF CORONARY ARTERIES

[76] Inventor: David F. Horrobin, 110 Pine Ave., West, Montreal, Canada, H2W 1R7

[21] Appl. No.: 38,938

[22] Filed: May 14, 1979

[30] Foreign Application Priority Data

May 26, 1978 [GB] United Kingdom ............... 23060/78

[51] Int. Cl.³ .................... A61K 31/405; A61K 31/47
[52] U.S. Cl. ..................................... 424/274; 424/258
[58] Field of Search ............................... 424/274, 258

[56] References Cited

PUBLICATIONS

Jugdutt, Circulation, vol. 59, No. 4, Apr. 1979, pp. 734–743.
Korbut, Chem. Abs., vol. 85, 1976, Ab. No. 85: 72383e.
McKeen, J. Clin. Invest., vol. 61, No. 2, May 1978, (rec'd. PTO, Apr. 7, 1978), pp. 1291–1297.
Karmazyn, Endocrinology, vol. 102, No. 4, Apr. 1978, pp. 1230–1236.
Afonso, J of Physiology, vol. 241, No. 2, 1974, pp. 299–308.
Martindale, The Extra Pharm., The Pharm. Press, London, 26th Ed., 1972, pp. 237–240.
Golding, British Med. J., iv, Dec. 5, 1970, p. 622.
McGinn, The NE J of Med., vol. 279, No. 8, Aug. 22, 1968, p. 436.
Baron, The NE J of Med., vol. 278, No. 23, Jun. 6, 1968, pp. 1291–1292.

*Primary Examiner*—Anna P. Fagelson
*Attorney, Agent, or Firm*—Schwartz, Jeffery, Schwaab, Mack, Blumenthal & Koch

[57] ABSTRACT

A method for the treatment or prophylaxis of angina pectoris or myocardial infarction which consists of administering indomethacin or chloroquine. It has been found that angina pectoris and myocardial infarction may be susceptible to treatment by administration of substances which will inhibit the synthesis or action of prostaglandins, which it is believed to be the effect of administering indomethacin or chloroquine.

2 Claims, 2 Drawing Figures

TREATMENT AND/OR PROPHYLAXIS OF SPASMS OF CORONARY ARTERIES

This invention relates to the treatment of heart disease, in particular the treatment of angina pectoris and myocardial infarction, and to pharmaceutical compositions for use therefor.

Angina pectoris is a syndrome in which pain originating in the heart occurs either at rest or more usually as a consequence of some form of physical or emotional stress such as exercise, cold or anger. It is currently believed to be due to a deficiency in the normal oxygen sypply to the heart, leading to the production of lactic acid and other pain producing substances. The reduced oxygen supply is due to the obstruction of the coronary arteries by some form of atherosclerosis. In some individuals even at rest the coronary arteries may be so obstructed that blood supply is inadequate and pain occurs. In others when physical or emotional stress leads to a need for increased pumping by the heart, the coronary blood vessels may be unable to open widely enough to cope with the increased need for oxygenated blood and again pain occurs.

Myocardial infarction is death of a portion of the heart muscle due to complete of near complete obstruction of a coronary artery supplying that portion. Mechanisms of obstruction which are believed to occur include formation of atheromatous deposits alone, embolisation (due to some solid material formed elsewhere being swept into the artery), occlusion of the vessel by some form of blood clot, or haemorrhage into the wall of the artery leading to the artery becoming closed. Clotting and haemorrhage are believed to occur mainly in vessels already damaged by atheroma. Closure of a coronary artery in any of these ways may lead to death of the subject by killing so much heart muscle that the heart can no longer function adequately as a pump or by causing the heart to go into an abnormal rhythm which also causes ineffective pumping.

Angina pectoris has generally hitherto heen treated chemotherapeutically using the following types of substances:

1. Nitrites, which act as coronary vasodilators and allow the coronary blood vessels to open to their maximum extent;
2. Propranolol and other beta-blocking substances, which are believed to interfere with the action of catecholamines on the heart, so limiting the work which the heart has to do and limiting its demand for oxygen, if the oxygen demand does not exceed the supply, pain will not occur; and
3. Drugs which will inhibit the development of cardiac arrhythmia as a result of the lack of oxygen. These drugs have so-called membrane-stabilizing or local anaesthetic properties, and thus they all block nerve conduction. They include propranolol (which thus has a dual action), ligonocaine (lidocaine), quinidine, procaine amide and related compounds.

The treatment of myocardial infarction is currently generally based on the prevention of any extension of blood clotting and on the prevention or correction of any cardiac arrhythmia. Thus, arrhythmia is treated by the administration of membrane stabilizing drugs and-/or by electrical defibrillation, and, less generally, blood-clotting is inhibited by the administration of anticoagulant drugs.

It has recently been suggested that angina pectoris is not simply due to a failure of adequate dilation of coronary vessels but may be caused by an active coronary vessel constriction so reducing blood flow to the affected part of the heart even below resting levels. It has also been suggested that in many cases myocardial infarction is due not to anatomical blocking of a coronary artery but to functional blocking due to a spasm of the coronary arteries.

Considerable interest has been shown in recent years concerning the metabolic effects of prostaglandins (PG's). It is believed that PGE 2 and related prostaglandins of the 2 series, such as PGF 2α and PGI 2, are synthesised from arachidonic acid via intermediate prostaglandin endoperoxides, arachidonic acid itself being synthesised from membrane phospholipids or dihomo-γ-linolenic acid. Simultaneously with the production of the final prostaglandins, the compound thromboxane A2 (TXA2) is also synthesised from the intermediate prostaglandin endoperoxides, and this compound acts in a "negative feedback" capacity in the synthetic route whereby it acts to regulate production of arachidonic acid from its precursors and also to regulate production of the intermediate prostaglandin endoperoxides from arachidonic acid.

Studies of the effects of prostaglandins and TXA2 on the heart have been reported, in which it is claimed that TXA2 is a coronary vasoconstrictor while the above prostaglandins have a relatively small activity or are (in the case of PGI2) powerful coronary dilators. It has also been claimed that PG's inhibit the formation of cardiac arrhythmia. I have now confirmed that TXA2 causes coronary vasoconstriction, but I have also found that in the levels likely to be found in vivo in the body (i.e. $10^{-12}$ to $10^{-8}$ M), PGE2, PGF2α and PGI2 also cause coronary vasoconstriction and cardiac arrhythmia. The previously reported vasodilating and antiarrhythmic effects only appearing at much higher concentrations than are found in vivo.

I therefore believe that the administration of substances which will inhibit the synthesis or action of prostaglandins may be useful in the treatment of angina pectoris and/or myocardial infarction.

Thus, according to one aspect of the present invention there is provided a method for the treatment and-/or prophylaxis of angina pectoris or myocardial infarction in a subject which comprises administering to the subject an effective amount of indomethacin or chloroquine.

Indomethacin causes inhibition of prostaglandin synthesis while chloroquine acts as a prostaglandin antagonist.

According to another aspect of the present invention I provide pharmaceutical compositions for use in the prophylaxis and/or treatment of angina pectoris or myocardial infarction which compositions comprise as active ingredient indomethacin or chloroquine. Such compositions may be formulated and prepared using pharmaceutical carriers and excipients conventional to the pharmaceutical art and may include other active ingredients.

The compounds for use in the method according to the invention may be administered by an oral, rectal or parenteral route, although they may be most conveniently administered intravenously or directly into the coronary circulation.

Suitable dosages of chloroquine and indomethacin for the relief or prevention of angina pectoris and/or myocardial infarction are 0.2 to 3 g and 50 to 500 mg respectively in one or more doses.

As indicated above the compounds may most conveniently be administered by an intravenous route. However, for emergency treatment in situations where intravenous administration is difficult or impossible, compositions containing from 0.2 to 3 g of chloroquine or 50 to 500 mg of indomethacin may be administered on one or more doses by an oral route.

In my studies, I have found that a reduced oxygen supply to the heart initially causes coronary vasodilation but if the hypoxia is severe or prolonged, the dilation passes off and coronary vasospasm develops. I have used this discovery to demonstrate that indomethacin and chloroquine can prevent or reverse such a spasm and may therefore be useful in the treatment of angina pectoris or myocardial infarction. My studies have also shown that indomethacin is a potent dilator of coronary arteries.

PHYSIOLOGICAL STUDY

Methods

3 Month (average 97 days) old male Wistar rates were used in the study. Hearts were removed from the etheranaesthetized animals and the aorta cannulated retrogradely (Langendorff Method). The coronary arteries were perfused at constant flow with a Watson-Marlowe peristaltic pump by Krebs-Henseleit buffer gassed with a 95% $O_2$/5% $CO_2$ mixture. For hypoxic perfusion the buffer was replaced with completely ungassed medium ($pO_2$ 20-30 mm Hg). The pH of the gassed medium was 7.4 and of the hypoxic medium 7.1. The temperature of the entire system was 37° C. The perfusion pressure was recorded via a side-arm off the aortic cannula. The flow (5 ml/g/min) was adjusted before starting the experiment to give an initial pressure of 75-100 mm Hg and not changed thereafter.

Results

Indomethacin was a potent dilator of coronary arteries in oxygenated hearts as shown by the results graphically respresented in FIG. 1, where the effect of increasing concentration of indomethacin on coronary perfusion pressure in the isolated rat hearts is shown. Each concentration was tested for 10 minutes.

Figure 2:
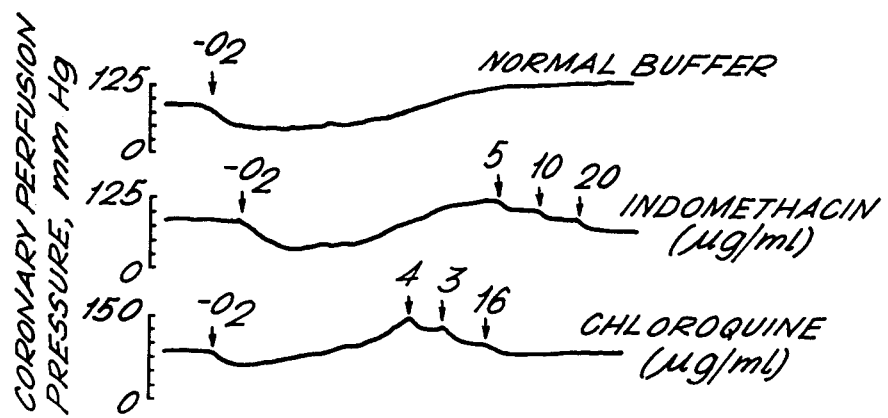

FIG. 2 graphically shows the effect on coronary perfusion pressure of isolated rat hearts during hypoxia in normal buffer (top) and after addition of indomethacin and chloroquine. It can be seen that indomethacin reversed hypoxia-induced coronary constriction, and chloroquine was effective at 4 μg/ml to reverse significantly ($p<0.05$) the rise in pressure (4 experiments) as well as to prevent it if present before constriction developed (2 experiments, not shown).

Figure 3:
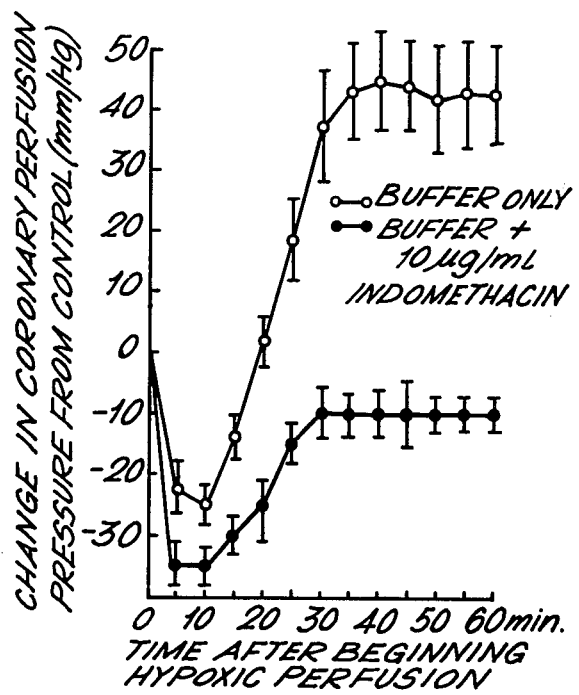

FIG. 3 graphically shows the effect of indomethacin (6 experiments) on the coronary artery response to hypoxia in isolated rat hearts, when the drug was present in the buffer before changing to hypoxic perfusion. It can be seen that the drug is capable of preventing the hypoxia-induced coronary constriction which develops with the buffer alone.

I claim:

1. A method for the treatment and/or prophylaxis of spasms of coronary arteries causing angina pectoris or myocardial infarction in a subject which method comprises administering to the subject an effective amount therefor of indomethacin.

2. A method according to claim 1 wherein indomethacin is administered in one or more doses in an amount of from 50 to 500 mg.

* * * * *